United States Patent [19]

Williams

[11] 4,338,947

[45] Jul. 13, 1982

[54] POSITIVE FIXATION HEART WIRE

[75] Inventor: Terrell M. Williams, Coon Rapids, Minn.

[73] Assignee: Medtronic, Inc., Minneapolis, Minn.

[21] Appl. No.: 202,978

[22] Filed: Nov. 3, 1980

[51] Int. Cl.³ .......................... A61B 5/04; A61N 1/04
[52] U.S. Cl. .................................. 128/642; 128/785; 128/419 P
[58] Field of Search .............................. 128/784–786, 128/419 P, 642

[56] References Cited

U.S. PATENT DOCUMENTS

| 3,035,583 | 5/1962 | Hirsch et al. | 128/784 X |
| 3,474,791 | 10/1969 | Bentor | 128/785 X |
| 4,010,756 | 3/1977 | DuMont et al. | 128/786 |
| 4,144,889 | 3/1979 | Tyers et al. | 128/418 |

FOREIGN PATENT DOCUMENTS 2846136  4/1980  Fed. Rep. of Germany .

OTHER PUBLICATIONS

Medtronic, Inc. Product Catalog Effective Apr. 15, 1979, "Temporary Leads" sheet.

Primary Examiner—Lee S. Cohen
Attorney, Agent, or Firm—John L. Rooney; Joseph F. Breimayer; Carl A. Forest

[57] ABSTRACT

A lead or heart wire for use in temporary electrical stimulation or monitoring of epicardial tissue. Positive fixation is accomplished by suturing the electrode to the tissue using an attached length of surgical thread and a curved needle. The heart wire is a tightly wound helix of wire insulated by a sheath. A needle, used for electrical connection to external equipment, is attached to the proximal end. Near the distal end, the conductor is bent into an "C" shape. The electrode is attached about midway along the top of the "C" shaped length of conductor. The length of surgical thread is attached to the proximal end of the conductor and exits the sheath through an aperture proximal to the "C" shape. The curved needle is attached to the distal end of the surgical thread. The heart wire may be readily removed after use by removing the surgical thread. The heart wire may be readily removed after use by removing the surgical thread, which is retracted into the conductor by pulling at its proximal end.

8 Claims, 4 Drawing Figures

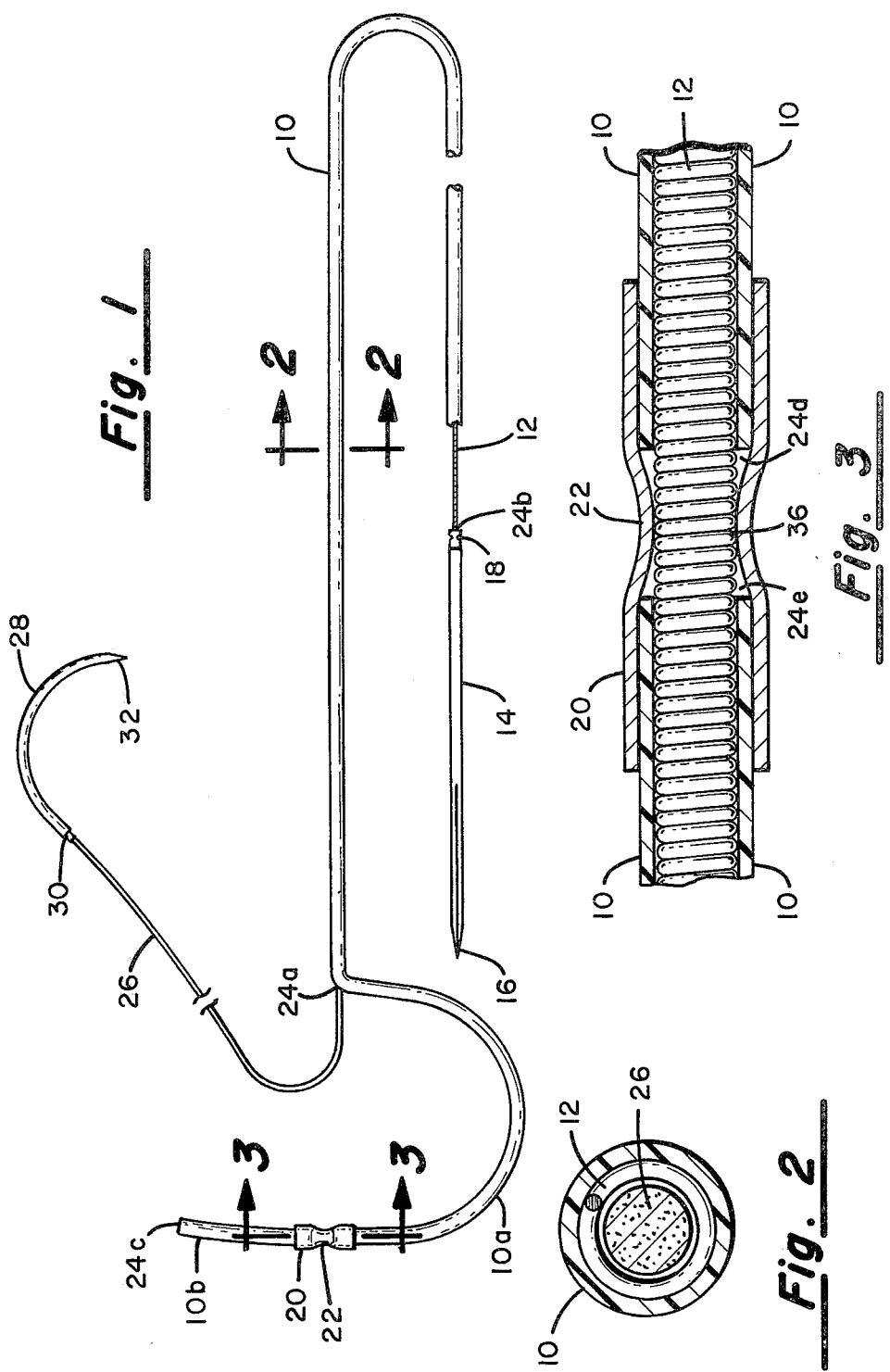

POSITIVE FIXATION HEART WIRE

BACKGROUND OF THE INVENTION

1. Field of the Invention

The present invention relates generally to a surgical electrode lead and more specifically relates to a heart wire for temporary application.

2. Description of the Prior Art

The use of temporary leads for pacing and monitoring purposes is quite common. Specially designed leads are used for such temporary applications which are much lighter and less durable than permanent leads since extended flex life is not required. It is still critical, however, that electrodes be properly affixed to tissue to permit the required transfer of electrical energy. This electrical contact must be established in a manner which permits convenient and safe removal of the lead with minimal permanent scarring and other effects. Furthermore, for epicardial applications, most permanent leads are more costly than is felt justified for temporary use.

Ackerman teaches construction of temporary leads for curing caridac arrest in U.S. Pat. Nos. 3,485,247 and 3,516,412. The former reference uses a hookshaped tip for affixing the lead whereas the latter uses resiliencey of shape. Neither of these techniques is suitable for most applications, however, as both leads are intended to be percutaneously inserted and actually puncture the myocardium. Because of the permanent effects of this technique, it is not useful under routine circumstances.

The primary method of affixing temporary epicardial leads is with sutures. Typically, this technique provides the greatest reliability with minimal permanent damage. Sutures were used in the earliest pacing applications for affixing all leads. U.S. Pat. No. 3,244,174, issued to Wessey, et al, teaches a lead whose electrodes are affixed using a suture pad.

U.S. Pat. No. 3,474,791, issued to Benton, teaches a lead having insulation removed at points which permit electrical contact. The lead may have a curved surgical needle attached directly to the distal end of the conductor for inserting the lead directly into the myocardium. Additional sutures are used to further attach the lead to the epicardium. U.S. Pat. No. 3,035,583, issued to Hirsch, et al teaches the use of sutures which are conductive.

These earlier suturing techniques for affixing the electrode to the myocardium lend themselves primarily to permanent implantation, since removal of the lead is difficult. For temporary applications, the lead must be easily removable and cause minimal permanent damage. Ideally, no portion of the lead should remain in the body after use.

SUMMARY OF THE INVENTION

The present invention provides a heart wire which is positively affixed to the epicardium to give good electrical conductivity and minimal mechanical movement. Yet the heart wire is rapidly removed when no longer needed leaving little permanent scarring. No portion remains after removal.

The temporary lead or heart wire has a needle connected to the proximal end for percutaneous connection to an external electrical device. The main body of the heart wire is a tightly wound helix of wire which serves as the conductor between the needle at the proximal end and the electrode. The helix is covered with an insulating sheath of silicon rubber or other body compatible material. The heart wire is sealed by filling with surgical silicon grease.

At a point near the distal end of the heart wire, the conductor is bent into a "C" shape. The electrode is attached to the conductor at about the midpoint of the top of the "C" shape. A length of surgical thread is permanently attached to the distal end of the needle. The surgical thread is located coaxially within the conductor between the proximal end of the sheath and an aperture located proximal to the the "C" shape. The surgical thread exits the lead at the aperture. A curved needle is attached to the distal end of the surgical thread.

Using the curved needle and the surgical thread, one suture is made proximal of the electrode. A second suture is made distal of the electrode. The surgical thread intermediate the first and second sutures holds the electrode in contact with the epicardium. The excess surgical thread is cut and removed. Rapid removal of the two sutures and the heart wire following use is accomplished by percutaneously pulling on the needle. The conductor stretches retracting the sutures into the lead.

BRIEF DESCRIPTION OF THE DRAWINGS

FIG. 1 is a view of a temporary lead or heart wire embodying the present invention.

FIG. 2 is a cross-sectional view of the lead.

FIG. 3 is a side sectional view of the electrode.

DETAILED DESCRIPTION OF THE PREFERRED EMBODIMENT

Figure 4:
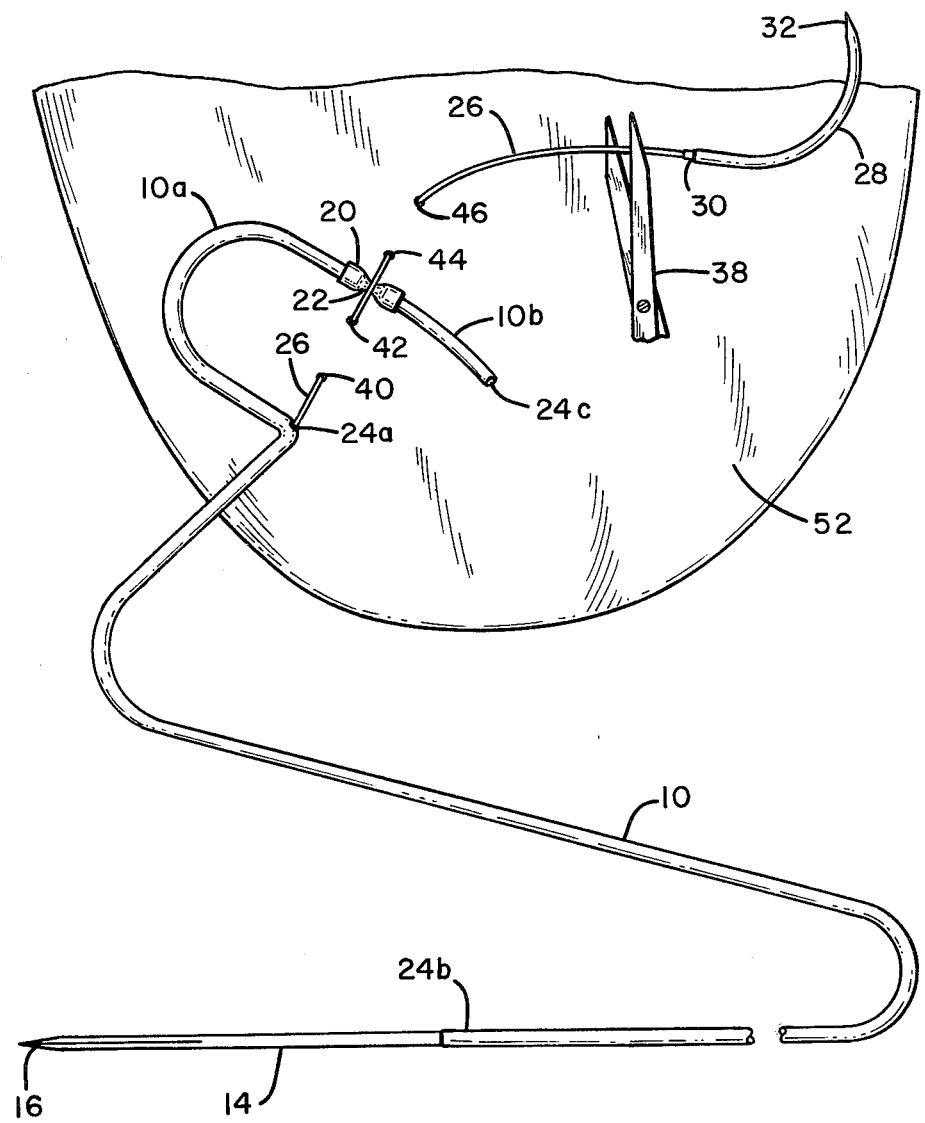
FIG. 4 shows suturing of the heart wire to epicardial tissue.

The preferred embodiment of the present invention is described herein along with those design details pertinent to that embodiment. Those skilled in the art will be able to readily apply this disclosure to other embodiments.

FIG. 1 shows a temporary lead or heart wire embodying the preferred mode of the present invention. The main body of the heart wire is relatively thin, being approximately 0.020 to 0.030 inches in diameter and is 50 cm long. Outer sheath 10 covering the body of the heart wire is a commonly used implantable insulator such as silicon rubber or polyurethane. It extends from the needle to the distal tip 24c. Conductor 12, within the main body of the heart wire, is coiled into a tightly wound helix extending from point 18 to 24c. The tightly wound helix configuration renders the main body of the heart wire extremely flexible. Conductor 12 is stainless steel or other wire being approximately 0.005 inches in diameter.

Conductor 12 is coupled to needle 14 by being crimped at connection point 18. Needle 14 is an electrical connector pin for coupling the heart wire to an external electrical device. Needle 14 has a point tip 16 for percutaneous connection to the external electrical device.

The distal end of outer sheath 10 is at point 24c which is also the distal end of the tightly wound helix. Distally from point 24a extends in a "C" shape as shown, having a bend 10a. Bend 10a is within a single plane giving the "C" shape as shown.

Electrode 20 is attached to conductor 12 about midway in the top of the "C" shape as shown. Attachment is made via crimp 22 as shown. To achieve a proper electrical connection a portion of sheath 10 is removed under electrode 20 enabling contact with conductor 12.

Surgical thread 26 is a commercially available suture material such as Surgilene. It is permanently attached to needle 14, at point 18 along with conductor 12. Surgical thread 26 is coaxially encased by conductor 12 from point 24b to 24a. At point 24a surgical thread 26 exits the main body of the lead through an aperture as shown. Needle 28 is permanently attached to the distal end of surgical thread 26 by crimp 30. Needle 28 is a surgical needle of about 8 mm radius of curvature having a point 32. Outer sheath 10 is sealed by the insertion of silicon grease or other similar material at point 24a and within conductor 12.

FIG. 2 is a cross sectional view of the heart wire. Conductor 12 is shown as a coil of wire. Surgical thread 26 is coaxially located wihin conductor 12. Sheath 10 encases conductor 12.

FIG. 3 is a sectional view of electrode 20. Notice that conductor 12 is continuous. Crimp 22 causes electrode 20 to frictionally enage conductor 12 and thereby becomes fixedly attached. A portion of sheath 10 is removed between point 24d and point 24e to enable electrode 20 to contact conductor 12 at crimp 22.

FIG. 4 shows suturing of the heart wire into position. Two sutures are made. A first suture between apertures 40 and 42 fixes point 24a of the main body of the heart wire to epicardial tissue 52. The second suture is from aperture 44 to aperture 46. Surgical thread 26 passes over electrode 20 and tightly engages crimp 22 holding electrode 20 firmly against epicardial tissue 52 by its stiffness.

After the second suture is complete, the excess of surgical thread 26 (and needle 28) is cut, using cutting tool 38. Being thus attached, electrode 20 will remain in good electrical contact with epicardial tissue 52 until removed. To remove the heart wire, the proximal end of sheath 10 is percutaneously moved proximal relative to conductor 12. This removes the two sutures. The heart wire may thereafter by easily withdrawn.

Having thus described the preferred embodiment of the present invention, it is apparent to those of ordinary skill in the art that many other practical embodiments are possible within the scope of the present invention.

What is claimed is:

1. A heart wire for maintaining electrical contact between an electrical device and body tissue comprising:
   an elongated conductor having a distal end and proximal end;
   an insulative sheath having a distal end and a proximal end and encasing said conductor;
   an electrode fixedly attached to said conductor intermediate the distal end and the proximal end of said conductor and which is exposed to the exterior of said insulative sheath;
   a length of surgical thread having a distal end and a proximal end which is fixedly attached to said sheath proximal to said electrode.

2. A heart wire according to claim 1 further comprising an electrical connector attached to said proximal end of said conductor.

3. A heart wire according to claim 2 wherein said conductor is formed into a tightly wound helix intermediate said electrical connector and said electrode.

4. A heart wire according to claim 3 further comprising a curved surgical needle fixedly attached to said distal end of said surgical thread.

5. A heart wire according to claim 3 or claim 4 wherein said conductor is further comprised of a "C" shaped bend, at least a portion of said "C" shaped bend being proximal to said electrode.

6. A heart wire according to claim 5 wherein said surgical thread is fixedly attached to said sheath proximal to said "C" shaped bend.

7. A heart wire according to claim 5 wherein said electrode further comprises means for engaging said surgical thread.

8. A heart wire according to claim 7 wherein said surgical thread is stiff whereby said thread may be engaged frictionally by said engaging means.

* * * * *